US006143718A

United States Patent [19]
Kolterman et al.

[11] Patent Number: 6,143,718
[45] Date of Patent: Nov. 7, 2000

[54] TREATMENT OF TYPE II DIABETES MELLUTIS WITH AMYLIN AGONISTS

[75] Inventors: Orville G. Kolterman, Poway; Robert G. Thompson, San Diego; John F. Mullane, Cardiff, all of Calif.

[73] Assignee: Amylin Pharmaceuticals, Inc., San Diego, Calif.

[21] Appl. No.: 08/483,188

[22] Filed: Jun. 7, 1995

[51] Int. Cl.$^7$ ........................... A61K 38/10; A61K 38/23
[52] U.S. Cl. .................................. 514/12; 514/4; 514/21
[58] Field of Search ..................................... 514/12, 21, 4

[56] References Cited

U.S. PATENT DOCUMENTS

| | | | |
|---|---|---|---|
| 5,124,314 | 6/1992 | Cooper | 514/4 |
| 5,175,145 | 12/1992 | Cooper . | |
| 5,234,906 | 8/1993 | Young et al. | 514/12 |
| 5,264,372 | 11/1993 | Beaumont et al. . | |
| 5,266,561 | 11/1993 | Cooper, et al. . | |
| 5,281,581 | 1/1994 | Cooper et al. . | |
| 5,321,008 | 6/1994 | Beaumont et al. | 514/4 |
| 5,367,052 | 11/1994 | Cooper et al. . | |
| 5,376,638 | 12/1994 | Young et al. . | |
| 5,686,411 | 11/1997 | Gaeta et al. | 514/12 |

FOREIGN PATENT DOCUMENTS

| | | |
|---|---|---|
| WO 93/10146 | 5/1993 | WIPO . |
| WO 95/07098 | 3/1995 | WIPO . |

OTHER PUBLICATIONS

Kolterman et al., "Infusion of Amylin Agonist AC–0137, Reduces Postprandial Hyperglycemia in Subjects with Type I Diabetes" Clinical Research 42 (1), pp 87A, Feb. 12, 1994.
Deems, et al. *Biochem. Biophys. Res. Commun.* 181:116–120 (1991).
Kanatsuka, et al., *FEBS Letters* 259:199–201 (1989).
Young, et al. *J. Cell Biochm.* 55S:12–18 (1994).
Alam, et al. *Biochem. Biophys. Res. Commun.* 179:134–139 (1991).
Beaumont, et al. *Mol. Pharmacol.* 44:493–497 (1993).
Brain, et al. *Eur. J. Pharmacol.* 183:2221 (1990).
Broderick, et al. *Biochem. Biophys. Res. Commun.* 177:932–938 (1991).
Chance, et al. *Brain Res.* 539:352–354 (1991).
Cooper, et al. *Proc. Natl. Acad. Sci. USA* 85:7763–7766 (1988).
Cooper, et al. *Proc. Natl. Acad. Sci.* 85:7763–7766 (1988).
Cooper, et al. *Proc. Natl. Acad. Sci.* 84:8628–8632 (1987).
Deems, et al. *Biochem. Biophys. Res. Commun.* 174:716–720 (1991).
Frontoni, et al. *Diabetes* 40:568–573 (1991).
Gedulin, et al. *Biochem. Biophys. Res. Commun.* 180:782–789 (1991).
Gill, et al. *Life Sciences* 48:703–710 (1991).
Gomez–Foix, et al. *Biochem J.* 276:607–610 (1991).
Hartter, et al. *Diabetologia* 34:52–54 (1991).
Huang, et al. *Hypertension* 19:I–101–I–109 (1991).
Koda, et al. *The Lancet* 339:1179–1180 (1992).
Koopmans, et al. *Diabetologia* 34:218–224 (1991).
Leighton, *Diabetologia* 35:801–802 (1992).
Leighton and Cooper *Nature*, 335:632–635 (1988).
Lupien and Young *Diabetes Nutrition and Metabolism—Clinical and Experimental* vol. 6(1), pp. 13–18 (1993).
Moore, et al. *Biochem. Biophys. Res. Commun.* 179:1–9 (1991).
Moyses and Kolterman *Amylin—A New Approach to Diabetes Therapy* (May 1995).
Ogawa, et al. *J. Clin. Invest.* 85:973–976 (1990).
Ohsawa, et al. *Biochem. Biophys. Res. Commun.* 160:961–967 (1989).
Phillips, et al. *J Nucl Med,* 33:1496–1500 (1992).
Rink, et al. *Trends Pharmacol. Sci.* 14:113–118 (1993).
Roden, et al. *Diabetologia* 35:116–1120 (1992).
Sanke, et al. *Diabetologia* 34:129–132 (1991).
Silvestre, et al. *Reg. Pept.* 31:23–31 (1991).
Stephens, et al. *Diabetes* 40:395–400 (1991).
The Diabetes Control and Complications Trial Research Group, *N. Eng. J. Med.* 329:977 (1993).
Young, et al. *Diabetologia* 38:642–648 (Jun. 1995).
Young, et al. *FEBS Letts.* 281:149–151 (1991).
Young et al. *Mol. Cell. Endocrinol.* 84:R1–R5 (1992).
Zaidi, et al., *J. Bone Mineral Res.* 5 (Suppl. 2) S76 (1990).
Young, et al. *J. Cell Biochm.* 55s:12–18 (1994).

*Primary Examiner*—Michael P. Woodward
*Assistant Examiner*—Abdel A. Mohamed
*Attorney, Agent, or Firm*—Lyon & Lyon LLP

[57] ABSTRACT

Methods for treating non-insulin-taking Type II diabetes mellitus which comprise administering a therapeutically effective amount of an amylin agonist.

21 Claims, 1 Drawing Sheet

FIGURE 1

TREATMENT OF TYPE II DIABETES MELLUTIS WITH AMYLIN AGONISTS

FIELD OF THE INVENTION

The present invention relates to medicine, and, more particularly, to amylin agonists and methods for the treatment of Type II diabetes mellitus by administering an amylin agonist.

BACKGROUND

Publications and other materials including patents and patent applications used to illuminate the specification are hereby incorporated by reference.

Amylin

Amylin is a 37 amino acid protein hormone. It was isolated, purified and chemically characterized as the major component of amyloid deposits in the islets of pancreases of human Type II diabetics (Cooper et al., *Proc. Natl. Acad. Sci., USA* 84:8628–8632 (1987)). The amylin molecule has two important post-translational modifications: the C-terminus is amidated, and the cysteines in positions 2 and 7 are cross-linked to form an N-terminal loop. Amylin is the subject of United Kingdom patent application Serial No. 8709871, filed Apr. 27, 1987, and corresponding U.S. Pat. No. 5,367,052, issued Nov. 22, 1994.

Amylin is a member of a family of related peptides which include CGRP and calcitonin (Rink et al., *Trends Pharmacol. Sci.* 14:113–118 (1993)). Amylin is primarily synthesized in pancreatic beta cells and is secreted in response to nutrient stimuli such as glucose and arginine. Moore et al., *Biochem. Biophys. Res. Commun.* 179:1–9 (1991); Kanatsuka et al., *FEBS Lett.* 259:199–201 (1989); Ogawa et al., *J. Clin. Invest.* 85:973–976 (1990); Gedulin et al., *Biochem. Biophys. Res. Commun.* 180:782–789 (1991).

In normal humans, fasting amylin levels from 1 to 10 pM and post-prandial levels of 5 to 20 pM have been reported (e.g., Hartter et al., *Diabetologia* 34:52–54 (1991); Sanke et al., *Diabetologia* 34:129–132 (1991)); Koda et al., *The Lancet* 339:1179–1180 (1992)). In obese, insulin-resistant individuals, however, post-food amylin levels can go higher, reaching up to about 50 pM, for example. For comparison, the values for fasting and post-prandial insulin are 20 to 50 pM, and 100 to 300 pM respectively in healthy people, with perhaps 3-to 4-fold higher levels in insulin-resistant people. In Type 1 diabetes, where beta-cells are destroyed, amylin levels are at or below the levels of detection and do not rise in response to glucose (Koda et al., *The Lancet* 339:1179–1180 (1992)). In normal mice and rats, basal amylin levels have been reported from 30 to 100 pM, while values up to 600 pM have been measured in certain insulin-resistant, diabetic strains of rodents (e.g., Huang et al., *Hypertension* 19:I-101–I-109 (1991)); Gill et al., *Life Sciences* 48:703–710 (1991).

The first discovered action of amylin was the reduction of insulin-stimulated incorporation of glucose into glycogen in rat skeletal muscle (Leighton et al., *Nature* 335:632–635 (1988)); the muscle was made "insulin-resistant". Subsequent work with rat soleus muscle ex-vivo and in vitro has indicated that amylin reduces glycogen-synthase activity, promotes conversion of glycogen phosphorylase from the inactive b form to the active a form, promotes net loss of glycogen (in the presence or absence of insulin), increases glucose-6-phosphate levels, and can increase lactate output (see, e.g., Deems et al., *Biochem. Biophys. Res. Commun.* 181:116–120 (1991)); Young et al., *FEBS Letts.* 281:149–151 (1991)).

It is believed that amylin acts through receptors present in plasma membranes. Beaumont et al., *Mol. Pharmacol.* 44:493–497 (1993). Amylin receptors and their use in various methods for screening and assaying for amylin agonist and antagonist compounds are described in U.S. Pat. No. 5,264,372, issued Nov. 23, 1993.

The biological actions of amylin relating to fuel metabolism are discussed in Young et al., *J. Cell. Biochem.* 555:12–18 (1994). While amylin has marked effects on hepatic fuel metabolism in vivo, there is no general agreement as to what amylin actions are seen in isolated hepatocytes or perfused liver. The available data do not support the idea that amylin promotes hepatic glycogenolysis, i.e., it does not act like glucagon (e.g., Stephens, et al., *Diabetes* 40:395–400 (1991)); Gomez-Foix et al., *Biochem J.* 276:607–610 (1991)). It has been suggested that amylin may act on the liver to promote conversion of lactate to glycogen and to enhance the amount of glucose able to be liberated by glucagon (see Roden et al., *Diabetologia* 35:116–120 (1992)). Thus, amylin could act there as an anabolic partner to insulin in liver, in contrast to its catabolic action in muscle.

In fat cells, contrary to its action in muscle, amylin has no detectable actions on insulin-stimulated glucose uptake, incorporation of glucose into triglyceride, $CO_2$ production (Cooper et al., *Proc. Natl. Acad. Sci.* 85:7763–7766 (1988)) epinephrine-stimulated lipolysis, or insulin-inhibition of lipolysis (Lupien and Young, *Diabetes Nutrition and Metabolism— Clinical and Experimental*, Vol. 6(1), pages 13–18 (1993)). Amylin thus exerts tissue-specific effects, with direct action on skeletal muscle, marked indirect (via supply of substrate) and perhaps direct effects on liver, while adipocytes appear "blind" to the presence or absence of amylin. No direct effects of amylin on kidney tissue have been reported.

It has also been reported that amylin can have marked effects on secretion of insulin. In isolated islets (Ohsawa et al., *Biochem. Biophys. Res. Commun.* 160:961–967 (1989)), in the perfused pancreas (Silvestre et al., *Reg. Pept.* 31:23–31 (1991)), and in the intact rat (Young et al., *Mol. Cell. Endocrinol.* 84:R1–R5 (1992)), various experiments indicate that amylin down-regulates insulin secretion. The perfused pancreas experiments point to selective down-regulation of the secretary response to glucose with sparing of the response to arginine. Other workers, however, have been unable to detect effects of amylin on isolated beta cells, on isolated islets, or in the whole animal (see Broderick et al., *Biochem. Biophys. Res. Commun.* 177:932–938 (1991) and references therein).

A striking effect of amylin in rodents at pharmacological dosages in vivo is stimulation of a sharp rise in plasma lactate, followed by a rise in plasma glucose (Young et al., *FEBS Letts.* 281:149–151 (1991)). Evidence indicates that the increased lactate provides substrate for glucose production and that amylin actions can occur independent of changes in insulin or glucagon. In "glucose clamp" experiments, amylin infusions cause "insulin resistance", both by reducing peripheral glucose disposal, and by limiting insulin-mediated suppression of hepatic glucose output (e.g., Frontoni et al., *Diabetes* 40:568–573 (1991)); Koopmans et al., *Diabetologia* 34:218–224 (1991)).

It has been shown that amylin agonists can slow gastric emptying (Young et al., *Diabetologia* (June 1995, in press), and is believed to contribute to their ability to reduce post-prandial hyperglycemia (Moyses and Kolterman, *Drugs of the Future* (May 1995). Methods for reducing gastric motility and slowing gastric emptying comprising the administration of an amylin agonist (including amylin) are the subject of United States patent application Ser. No. 08/118,381, filed Sep. 7, 1993, and U.S. patent application Ser. No. 08/302,069, filed Sep. 7, 1994 (and corresponding PCT application, Publication No. WO 95/07098, published Mar. 16, 1995).

Non-metabolic actions of amylin include vasodilator effects which may be mediated by interaction with CGRP vascular receptors. (Brain et al., *Eur. J. Pharmacol.* 183:2221 (1990). It has also been reported that amylin markedly increases plasma renin activity in intact rats when given subcutaneously in a manner that avoids any disturbance of blood pressure. Methods for treating renin-related disorders with amylin antagonists are described in U.S. Pat. No. 5,376,638, issued Dec. 27, 1994.

Injected into the brain, amylin has been reported to suppress food intake (e.g., Chance et al., *Brain Res.* 539:352–354 (1991)), an action shared with CGRP and calcitonin. The effective concentrations at the cells that mediate this action are not known. Amylin has also been reported to have effects both on isolated osteoclasts where it caused cell quiescence, and in vivo where it was reported to lower plasma calcium by up to 20% in rats, in rabbits, and in humans with Paget's disease (see, e.g., Zaidi et al., *J. Bone Mineral Res.* 5(Suppl. 2) 576 (1990). From the available data, amylin seems to be 10 to 30 times less potent than human calcitonin for these actions. Interestingly, it was reported that amylin appeared to increase osteoclast cAMP production but not to increase cytosolic $Ca^{2+}$, while calcitonin does both (Alam et al., *Biochem. Biophys. Res. Commun.* 179:134–139 (1991)). It was suggested, though not established, that calcitonin may act via two receptor types and that amylin may interact with only one of these.

Diabetes Mellitus

Diabetes mellitus is a serious metabolic disease that is defined by the presence of chronically elevated levels of blood glucose. Classic symptoms of diabetes mellitus in adults are polyuria, polydipsia, ketonuria, rapid weight loss together with elevated levels of plasma glucose. Normal fasting plasma glucose concentrations are less than 115 milligrams per deciliter. In diabetic patients, fasting concentrations are found to be over 140 milligrams per deciliter. In general, diabetes mellitus develops in response to damage to the beta cells of the pancreas. This damage can result from primary diabetes mellitus, in which the beta cells are destroyed by the autoimmune system, or as a secondary diabetic response to other primary diseases, such as pancreatic disease, hormonal abnormalities other than lack of insulin action, drug or chemical induction, insulin receptor abnormalities, genetic syndromes or others. Primary diabetes mellitus can be classified as Type I diabetes (also called insulin-dependent diabetes mellitus or IDDM) and Type II diabetes mellitus (also called non-insulin dependent diabetes mellitus or NIDDM).

Type I (juvenile onset or insulin-dependent) diabetes is a well-known hormone deficient state, in which the pancreatic beta cells appear to have been destroyed by the body's own immune defense mechanisms. Patients with Type I diabetes mellitus have little or no endogenous insulin secretory capacity. These patients develop extreme hyperglycemia. Type I diabetes was fatal until the introduction of insulin replacement therapy some 70 years ago—first using insulins from animal sources, and more recently, using human insulin made by recombinant DNA technology. As discussed above, it is now clear that the destruction of beta cells in Type I diabetes leads to a combined deficiency of two hormones, insulin and amylin. When pancreatic cells are destroyed, the capacity to secrete insulin and amylin is lost. Type I diabetic subjects have reported amylin levels that are either undetectable or at the lower limit of detection, and which fail to increase in response to a glucose challenge. Koda, *The Lancet* 339:1179 (1992).

The nature of the lesion of the pancreatic beta cells in Type II diabetes is not clear. Unlike the pancreatic beta cells in Type I diabetics, the beta cells of Type II diabetics retain the ability to synthesize and secrete insulin and amylin.

Type II diabetes is characterized by insulin and resistance, i.e., a failure of the normal metabolic response of peripheral tissues to the action of insulin. In other words, insulin resistance is a condition where the circulating insulin produces a subnormal biological response. In clinical terms, insulin resistance is present when normal or elevated blood glucose levels persist in the face of normal or elevated levels of insulin. The hyperglycemia associated with Type II diabetes can sometimes be reversed or ameliorated by diet or weight loss sufficient to restore the sensitivity of the peripheral tissues to insulin. Indeed, Type II diabetes mellitus is often characterized by hyperglycemia in the presence of higher than normal levels of plasma insulin. Progression of Type II diabetes mellitus is associated with increasing concentrations of blood glucose and coupled with a relative decrease in the rate of glucose-induced insulin secretion. Thus, for example, in late- stage Type II diabetes mellitus, there may be an insulin deficiency.

The primary aim of treatment in all forms of diabetes mellitus is the same, namely the reduction of blood glucose concentrations to as near normal as possible, thereby minimizing both the short- and long-term complications of the disease. Tchobroutsky, *Diabetologia* 15:143–152 (1978). The linkage between the extent of hyperglycemia in diabetics and the ensuing long-term complications was further confirmed in the recently completed Diabetes Control and Complications Trial (DCCT) undertaken by the National Institutes of Health. The Diabetes Control and Complications Trial Research Group, *N. Eng. J. Med.* 329:977 (1993). The DCCT was conducted over a 10-year period at 29 clinical centers around the United States and Canada, and showed that lowering mean blood glucose concentrations in Type I diabetics reduced end-organ complications. The development of retinopathy was reduced by 76%, the progression of retinopathy by 54%, and there was an amelioration of the markers of renal disease (proteinuria, albuminuria). The development of significant neuropathic changes was also reduced.

The treatment of Type I diabetes necessarily involves the administration of replacement doses of insulin, administered by the parenteral route. In combination with the correct diet and self-blood glucose monitoring, the majority of Type I diabetics can achieve a certain level of control of blood glucose.

In contrast to Type I diabetes, treatment of Type II diabetes frequently does not require the use of insulin. Institution of therapy in Type II diabetes usually involves a trial of dietary therapy and lifestyle modification, typically for 6–12 weeks in the first instance. Features of a diabetic diet include an adequate but not excessive total calorie intake, with regular meals, restriction of the content of saturated fat, a concomitant increase in the polyunsaturated fatty acid content, and an increased intake of dietary fiber. Lifestyle modifications include the maintenance of regular exercise, as an aid both to weight control and also to reduce the degree of insulin resistance. If after an adequate trial of diet and lifestyle modifications, fasting hyperglycemia persists, then a diagnosis of "primary diet failure" may be made, and either a trial of oral hypoglycemic therapy or direct institution of insulin therapy will be required to produce blood glucose control and, thereby, to minimize the complications of the disease. Type II diabetics who fail to respond to diet and weight loss may respond to therapy with oral hypoglycemic agents such as sulfonylureas or biguanides. Insulin therapy, however, is used to treat other patients with Type II diabetes, especially those who have undergone primary dietary failure and are not obese, or those who have undergone both primary diet failure and secondary oral hypoglycemic failure.

The use of amylin agonists in the treatment of diabetes mellitus has been described in U.S. Pat. Nos. 5,124,314 and 5,175,145. Excess amylin action mimics key features of Type II diabetes and amylin blockade has been proposed as a novel therapeutic strategy. U.S. Pat. No. 5,266,561, issued Nov. 30, 1993, and U.S. Pat. No. 5,281,581, issued Jan. 25, 1994, disclose the treatment of Type II diabetes and insulin resistance with amylin antagonists.

It has previously been reported that infusion of the amylin agonist, $^{25,28,29}$Pro-h-amylin, decreased post-prandial glucose concentrations in Type I diabetics. Moyses & Kolterman, *Drugs of the Future* (May 1995). In a single blind crossover study in 6 male subjects with Type I diabetes, a 2-hour infusion of the amylin agonist, $^{25,28,29}$Pro-h-amylin at a rate of 150 µg/hr was reported to significantly decrease post-prandial hyperglycemia following ingestion of a mixed meal. This effect was confirmed in a second study which employed an infusion rate of 50 µg/hr for 5 hours in 9 subjects with Type I diabetes. A nutrient challenge was given either orally (in the form of a Sustacal® meal) or as an intravenous glucose load of 300 mg/kg. Administration of $^{25,28,29}$Pro-h-amylin reportedly led to a significant decrease in post-prandial glucose excursion after the oral Sustacal® meal, but not after the intravenous administration of glucose, consistent with an effect to delay gastric emptying and thus the gastrointestinal absorption of nutrients. In a further double-blind, placebo-controlled study, self-injected $^{25,28,29}$Pro-h-amylin, taken before meals thrice daily, also led to reduced glucose excursion after a test meal. The patients continued their usual insulin regime. In the third study, a statistically significant effect was seen with a dose of 30 µg of the amylin agonist.

SUMMARY OF THE INVENTION

We have discovered that, unexpectedly, non-insulin- taking Type II diabetic patients may be treated by the administration of an amylin agonist in order to lower their blood glucose concentrations. We have also discovered that treatment of non-insulin-taking Type II diabetic patients with an amylin agonist is particularly beneficial for those patients having an HbA1c value above normal.

In one aspect, the present invention is directed to a method for the treatment of a non-insulin-taking Type II diabetic subject comprising administering a therapeutically effective amount of an amylin agonist. By "non-insulin-taking Type II diabetic subject" is meant a subject who has Type II diabetes mellitus, but whose diabetes is currently being managed without the use of insulin, for example, by any combination of diet, exercise, modification of lifestyle, or use of oral hypoglycemic agents, such as biguanides and sulfonylureas. Diagnosis of patients afflicted with Type II diabetes is well within the ability and knowledge of one skilled in the art. For example, individuals over the age of 35 who have symptoms of polydipsia, polyuria, polyphagia (with or without weight loss) coupled with elevated plasma glucose concentrations and without a history of ketoacidosis are generally considered within the diagnosis of Type II diabetes mellitus. The presence of obesity, a positive family history for Type II diabetes and normal or elevated fasting plasma insulin and c-peptide concentrations are additional characteristics of most patients with Type II diabetes mellitus. By "therapeutically effective amount" is meant an amount, either in single or multiple doses, which beneficially reduces plasma glucose concentrations in a subject afflicted with Type II diabetes mellitus.

In a preferred embodiment, the present invention is directed to a method for the treatment of a non-insulin-taking Type II diabetic subject comprising administering a therapeutically effective amount of an amylin agonist wherein the subject has a HbA1c value above the upper end of the range of HbA1c values for normal subjects. HbA1c represents a post-translational modification of hemoglobin which occurs by a non-enzymatic process whereby glucose becomes attached to hemoglobin A, and typically reflects the average plasma glucose concentration over the preceding 120 days, the average lifespan of a red blood cell. The upper end of the normal range for HbA1c values, that is, the upper end of the range for normal non-diabetic subjects, is generally understood to be from about 6.0% to about 7.5%. In another preferred embodiment, the subject has an HbA1c value of at least about 8%.

In another aspect, the present invention is directed to a method of lowering blood glucose in a non-insulin-taking Type II diabetic subject comprising administering to said subject a blood glucose-lowering amount of an amylin agonist. A glucose-lowering amount of an amylin agonist will preferably range from between about 0.05 µg/kg/day to about 10 µg/kg/day, more preferably, between about 0.05 µg/kg/day to about 6 µg/kg/day, and even more preferably, between about 1.0 µg/kg/day to about 4 µg/kg/day. For example, an effective blood glucose lowering amount of $^{25,28,29}$Pro-h-amylin (AC137) will generally vary from about 0.05 µg/kg/day to about 10 µg/kg/day, preferably 0.1 µg/kg/day to about 6.0 µg/kg/day. A dose of from about 1.0 µg/kg/day to about 4.0 µg/kg/day is preferred. In a preferred embodiment, the subject has an HbA1c value above the upper end of the normal range of HbA1c values for normal subjects. In another preferred embodiments of the present invention, the subject has an HbA1c value of at least about 8%.

In preferred embodiments of the present invention, the amylin agonist is selected from group consisting of $^{25,28,29}$Pro-h-amylin (AC137), s-calcitonin (salmon calcitonin) and h-amylin. Particularly preferred is $^{25,28,29}$Pro-h-amylin (AC137).

Administration of amylin agonists may be by various routes, including subcutaneously, intramuscularly, nasally or transdermally.

BRIEF DESCRIPTION OF THE DRAWINGS

The invention will be further described with reference to the accompanying drawings in which.

DETAILED DESCRIPTION OF THE INVENTION

Amylin agonist agents may be identified by activity in the receptor binding and soleus muscle assays described below.

Amylin agonist activity of compounds may also be assessed by the ability to induce hypercalcemia and/or hyperglycemia in mammals, or to reduce post-prandial plasma glucose levels, as described herein.

The nomenclature of various amylin agonist compounds useful in the present invention can be used to indicate both the peptide that the sequence is based on and the modifications made to any basic peptide amylin sequence, such as human amylin. An amino acid preceded by a superscript number indicates that the named amino acid replaces the amino acid normally present at the amino acid position of the superscript in the basic amino acid sequence. For example, "$^{18}$Arg$^{25,28}$Pro-h-amylin" refers to a peptide based on the sequence of "h-amylin" or "human-amylin" having the following substitutions: Arg replacing His at residue 18, Pro replacing Ala at residue 25 and Pro replacing Ser at residue 28. The term "des-$^1$Lys-h-amylin" refers to a peptide based on the sequence of human amylin, with the first, or N-terminal, amino acid deleted.

Preferred amylin agonist compounds des-$^1$Lys-hamylin, $^{28}$Pro-h-amylin, $^{25,28,29}$Pro-h-amylin, $^{18}$Arg$^{25,28}$Pro-h-amylin, and des-$^1$Lys$^{18}$Arg$^{25,28}$Pro-h-amylin, all show amylin activity in vivo in treated test animals, provoking marked hyperlactemia followed by hyperglycemia. In addition to having activities characteristic of amylin, certain preferred compounds have also been found to possess more desirable solubility and stability characteristics when compared to human amylin. These preferred compounds include $^{25}$Pro$^{26}$Val$^{28,29}$Pro-h-amylin, $^{25,28,29}$Pro-h-amylin (also referred to herein as "AC-0137"), and $^{18}$Arg$^{25,28}$Pro-h-amylin.

The methods of the present invention employ an amylin agonists, including amylin or an amylin agonist analogue, for example, amylin receptor agonist analogues such as $^{18}$Arg$^{25,28}$Pro-h-amylin, des-$^1$Lys$^{18}$Arg$^{25,28}$Pro-h-amylin, $^{18}$Arg$^{25-28,29}$Pro-h-amylin, des-$^1$Lys$^{18}$Arg$^{25,28,29}$Pro-h-amylin, $^{25,28-29}$Pro-h-amylin, des-$^1$Lys$^{25,28,29}$Pro-h-amylin, and $^{25}$Pro$^{26}$Val$^{25,28}$Pro-h-amylin. Examples of other suitable amylin agonist analogues include:

$^{23}$Leu$^{25}$Pro$^{26}$Val$^{28,29}$Pro-h-amylin;

$^{23}$Leu$^{25}$Pro$^{26}$Val$^{28}$Pro-h-amylin;

des-$^1$Lys$^{23}$Leu$^{25}$Pro$^{26}$Val$^{28}$Pro-h-amylin;

$^{18}$Arg$^{23}$Leu$^{25}$Pro$^{26}$Val$^{28}$Pro-h-amylin;

$^{18}$Arg$^{23}$Leu$^{25,28,29}$Pro-h-amylin;

$^{18}$Arg$^{23}$Leu$^{25,28}$Pro-h-amylin;

$^{17}$Ile$^{23}$Leu$^{25,28,29}$Pro-h-amylin;

$^{17}$Ile$^{25,28,29}$Pro-h-amylin;

des-$^1$Lys$^{17}$Ile$^{23}$Leu$^{25,28,29}$Pro-h-amylin;

$^{17}$Ile$^{18}$Arg$^{23}$Leu-h-amylin;

$^{17}$Ile$^{18}$Arg$^{23}$Leu$^{26}$Val$^{29}$Pro-h-amylin;

$^{17}$Ile$^{18}$Arg$^{23}$Leu$^{25}$Pro$^{26}$Val$^{28,29}$Pro-h-amylin;

$^{13}$Thr$^{21}$His$^{23}$Leu$^{26}$Ala$^{28}$Leu$^{29}$Pro$^{31}$Asp-h-amylin;

$^{13}$Thr$^{21}$His$^{23}$Leu$^{26}$Ala$^{29}$Pro$^{31}$Asp-h-amylin;

des-$^1$Lys$^{13}$Thr$^{21}$His$^{23}$Leu$^{26}$Ala$^{28}$Pro$^{31}$Asp-h-amylin;

$^{13}$Thr$^{18}$Arg$^{21}$His$^{23}$Leu$^{26}$Ala$^{29}$Pro$^{31}$Asp-h-amylin;

$^{13}$Thr$^{18}$Arg$^{21}$His$^{23}$Leu$^{28,29}$Pro$^{31}$Asp-h-amylin; and, $^{13}$Thr$^{18}$Arg$^{21}$His$^{23}$Leu$^{25}$Pro$^{26}$Ala$^{28,29}$Pro$^{31}$Asp-h-amylin.

Still further amylin agonists including amylin agonist analogues are disclosed, and methods for making and using amylin agonists are further specified, in commonly owned in U.S. patent application, entitled "Novel Amylin Agonist Peptides and Uses Therfor" filed May 30, 1995 (docket no. 213/080) and corresponding PCT application Publication No. WO 93/10146, published May 27, 1993, the disclosures of which are hereby incorporated by this reference. These agonists are useful in reducing blood glucose concentrations in a non-insulin-using Type II diabetic subject.

The activity of amylin agonists may be evaluated using certain biological assays described herein. The receptor binding assay can identify both candidate amylin agonists and antagonists and can be used to evaluate binding, while the soleus muscle assay can be used to distinguish between amylin agonists and antagonists. Preferably, agonist compounds exhibit activity in the receptor binding assay on the order of less than about 1 to 5 nM, preferably less than about 1 nM and more preferably less than about 50 pM. In the soleus muscle assay these compounds preferably show $EC_{50}$ values on the order of less than about 1 to 10 micromolar.

The receptor binding assay is described in U.S. Pat. No. 5,264,372, issued Nov. 23, 1993, the disclosure of which is incorporated herein by reference. The receptor binding assay is a competition assay which measures the ability of compounds to bind specifically to membrane-bound amylin receptors. A preferred source of the membrane preparations used in the assay is the basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand are analyzed by computer, using analyses by nonlinear regression to a 4-parameter logistic equation (Inplot program; GraphPAD Software, San Diego, Calif.) or the ALLFIT program of DeLean et. al. (ALLFIT, Version 2.7 (NIH, Bethesda, Md. 20892)). Munson, P. and Rodbard, D., *Anal. Biochem.* 107:220–239 (1980).

Assays of biological activity of amylin agonists, including amylin agonist analogue preparations, in the soleus muscle are performed using previously described methods (Leighton, B. and Cooper, G. J. S., *Nature*, 335:632–635 (1988); Cooper, G. J. S., et al. *Proc. Natl. Acad. Sci. USA* 85:7763–7766 (1988)). In summary, amylin agonist activity is assessed by measuring the inhibition of insulin-stimulated glycogen synthesis in soleus muscle. Amylin antagonist activity is assessed by measuring the resumption of insulin-stimulated glycogen synthesis in the presence of 100 nM rat amylin and an amylin antagonist. Concentrations of peptide dissolved in carrier-free buffers are determined by quantitative amino acid analysis, as described therein. The ability of compounds to act as agonists in this assay is determined by measuring $EC_{50}$ values. Standard errors are determined by fitting of sigmoidal dose response curves using a four parameter logistic equation (De Lean, A., Munson, P. J., Guardabasso, V. and Rodbard, D. (1988) ALLFIT, Version 2.7, National Institute of Child Health and Human Development, N.I.H. Bethesda, Md., 1 diskette). A number of amylin agonists have been characterized using these biological assays. The compounds $^{18}$Arg$^{25,28}$Pro-h-amylin, des$^1$Lys$^{18}$Arg$^{25,28}$Pro-h-amylin, $^{18}$Arg$^{25,28,29}$Pro-h-amylin, des-$^1$Lys$^{18}$Arg $^{25,28,29}$Pro-h-amylin, $^{25,28,29}$Pro-h-amylin, des-$^1$Lys$^{25,28,29}$Pro-h-amylin, and $^{25}$Pro$^{26}$Val$^{25,28}$Pro-h-amylin were all found to compete with amylin in the receptor binding assay. These compounds have negligible antagonist activity as measured by the soleus muscle assay and were shown to act as amylin agonists.

Effects of amylins or amylin agonists on gastric motility can be identified, evaluated, or screened for using the methods described in U.S. application Ser. No. 08/118,381, filed Sep. 7, 1993, and U.S. application Ser. No. 08/302,069, filed Sep. 7, 1994 (corresponding to PCT Application, Publication No. WO 95/07098), the disclosures of which are hereby incorporated by reference, or other art-known or equivalent methods for determining gastric motility. One such method for use in identifying or evaluating the ability of a compound to slow gastric motility, comprises: (a) bringing together a test sample and a test system, said test sample comprising one or more test compounds, and said test system comprising a system for evaluating gastric motility, said system being characterized in that it exhibits, for example, elevated plasma glucose in response to the introduction to said system of glucose or a meal; and, (b) determining the presence or amount of a rise in plasma glucose in said system. Positive and/or negative controls may be used as well. Optionally, a predetermined amount of amylin antagonist (e.g., $^{8-32}$salmon calcitonin) may be added to the test system.

Amylin agonists such as those described above are prepared using standard solid-phase peptide synthesis techniques and preferably an automated or semiautomated peptide synthesizer. Typically, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer are purchased from Applied Biosystems Inc. (Foster City, Calif.), unless otherwise indicated. The side-chain protected amino acids are purchased from Applied Biosystems, Inc. and include the following: Boc-Arg(Mts), Fmoc-Arg(Pmc), Boc-Thr(Bzl), Fmoc-Thr(t-Bu), Boc-Ser (Bzl), Fmoc-Ser(t-Bu), Boc-Tyr(BrZ), Fmoc-Tyr(t-Bu), Boc-Lys(Cl-Z), Fmoc-Lys(Boc), Boc-Glu(Bzl), Fmoc-Glu (t-Bu), Fmoc-His(Trt), Fmoc-Asn(Trt), and Fmoc-Gln(Trt). Boc-His(BOM) is purchased from Applied Biosystems, Inc. or Bachem Inc. (Torrance, Calif.). Anisole, methylsulfide, phenol, ethanedithiol, and thioanisole are obtained from Aldrich Chemical Company (Milwaukee, Wis.). Air Products and Chemicals (Allentown, Pa.) supplies HF. Ethyl ether, acetic acid and methanol are purchased from Fisher Scientific (Pittsburgh, Pa.).

Solid phase peptide synthesis is carried out with an automatic peptide synthesizer (Model 430A, Applied Biosystems Inc., Foster City, Calif.) using the NMP/HOBt (Option 1) system and Tboc or Fmoc chemistry (see, Applied Biosystems User's Manual for the ABI 430A Peptide Synthesizer, Version 1.3B Jul. 1, 1988, section 6, pp. 49–70, Applied Biosystems, Inc., Foster City, Calif.) with capping. Boc-peptide-resins are cleaved with HF (−5° C. to 0° C., 1 hour). The peptide is extracted from the resin with alternating water and acetic acid, and the filtrates were lyophilized. The Fmoc-peptide resins are cleaved according to standard methods (*Introduction to Cleavage Techniques*, Applied Biosystems, Inc., 1990, pp. 6–12). Some peptides are also assembled using an Advanced Chem Tech Synthesizer (Model MPS 350, Louisville, Ky.). Peptides are purified by RP-HPLC (preparative and analytical) using a Waters Delta Prep 3000 system. A C4, C8 or C18 preparative column (10μ, 2.2×25 cm; Vydac, Hesperia, Calif.) is used to isolate peptides, and purity is determined using a C4, C8 or C18 analytical column (5μ, 0.46×25 cm; Vydac). Solvents (A=0.1% TFA/water and B=0.1% TFA/CH$_3$CN) are delivered to the analytical column at a flowrate of 1.0 ml/min and to the preparative column at 15 ml/min. Amino acid analyses are performed on the Waters Pico Tag system and processed using the Maxima program. The peptides are hydrolyzed by vapor-phase acid hydrolysis (115° C., 20–24 h). Hydrolysates are derivatized and analyzed by standard methods (Cohen, S. A., Meys, M., and Tarrin, T. L. (1989), *The Pico Tag Method: A Manual of Advanced Techniques for Amino Acid Analysis*, pp. 11–52, Millipore Corporation, Milford, Mass.). Fast atom bombardment analysis is carried out by M-Scan, Incorporated (West Chester, Pa.). Mass calibration is performed using cesium iodide or cesium iodide/glycerol. Plasma desorption ionization analysis using time of flight detection is carried out on an Applied Biosystems Bio-Ion 20 mass spectrometer.

Peptide compounds useful in the claimed methods also be prepared using recombinant DNA techniques, using methods now known in the art. See, e.g., Sambrook et al., *Molecular Cloning: A Laboratory Manual*, 2d Ed., Cold Spring Harbor (1989).

The compounds referenced above form salts with various inorganic and organic acids and bases. Such salts include salts prepared with organic and inorganic acids, for example, HCl, HBr, H$_2$SO$_4$, H$_3$PO$_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, and alkali earth salts, e.g. calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Compositions useful in the invention may conveniently be provided in the form of formulations suitable for parenteral (including, intramuscular and subcutaneous) or nasal or transdermal, and/or suitably encapsulated or otherwise prepared by another known methods for oral administration. A suitable administration format may best be determined by a medical practitioner for each patient individually. Suitable pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988).

Compounds useful in the invention can be provided as parenteral compositions for injection or infusion. Preferably, they are dissolved in an aqueous carrier, for example, in an isotonic buffer solution at a pH of about 4.3 to 7.4. These compositions may be sterilized by conventional sterilization techniques, or may be sterile filtered. The compositions may contain pharmaceutically acceptable auxiliary substances as required to stabilize the formulation, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions. If desired, solutions of the above compositions may be thickened with a thickening agent such as methyl cellulose.

Compositions useful in the invention are prepared by mixing the ingredients following generally accepted procedures. For example, the selected components may be mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of an amylin agonist, which will be effective in one or multiple doses to control blood glucose at the selected level. Therapeutically effective amounts of an amylin agonist are those that decrease post-prandial blood glucose levels, preferably to no lower than about 5 to 6 mM or such that blood glucose levels are reduced as desired. In diabetic or glucose intolerant individuals, plasma glucose levels are higher than in normal individuals. In such individuals, beneficial reduction or "smoothing" of post-prandial blood glucose levels, may be obtained. As will be recognized by those in the field, in determining an effective dose for a particular subject, a number of factors are considered, including without limitation the patient's size, age, and general health, the degree of or involvement or the severity of the disease, the response of the individual patient, the particular compound administered, the mode of administration, the bioavailability characteristics of the preparation administered, the dose regimen selected and the use of concomitant medication.

The effective daily dose of amylin agonists, including $^{18}Arg^{25,28}$Pro-h-amylin, des-$^{1}Lys^{18}Arg^{25,28}$Pro-h-amylin, $^{18}Arg^{25,28,29}$Pro-h-amylin, des-$^{1}Lys^{18}Arg^{-25,28,29}$Pro-h-amylin, $^{25,28,29}$Pro-h-amylin, des-$^{1}Lys^{25,28,29}$Pro-h-amylin, and $^{25}Pro^{26}Val^{25,28}$Pro-h-amylin, will typically be in the range of 0.05 µg/kg/day to about 10 µg/kg/day, preferably about 0.05 µg/kg/day to about 6.0 µg/kg/day and more preferably about 1.0 µg/kg/day to about 4.0 µg/kg/day administered in a single or divided doses. The exact dose to be administered is determined by the attending clinician and is dependent upon where the particular compound lies within the above quoted range, as well as upon the age, weight and condition of the individual. Administration should begin at the first sign of symptoms or shortly after diagnosis of diabetes mellitus. Administration may be by injection, preferably subcutaneous or intramuscular. Administration may also be nasally or transdermally. Orally active compounds may be taken orally, however dosages should be adjusted based on their potencies and bioavailabilities, as appropriate.

The following Example is illustrative, but not limiting of the methods of the present invention. Other suitable amylin agonist compounds that may be modified or adapted for use in the claimed methods are also appropriate and are within the spirit and scope of the invention.

EXAMPLE

A single-blind, placebo-controlled randomized, two-period crossover clinical trial was performed to assess the effects of microinfusion of the amylin agonist, $^{25,28,29}$Pro-h-amylin (AC137) on patients with Type II diabetes mellitus following a standardized oral test meal.

Patients who satisfied the screening requirements were randomized and participated in an investigation period which consisted of an acclimatization day (Study Day 1) followed by two treatment days (Study Days 2 and 3). Fourteen male and 10 female patients were enrolled in the trial Twelve patients were randomized to placebo/AC137 and 12 patients were randomized to AC137/placebo. Each study drug group had 6 insulin-treated patients and 6 non-insulin-treated patients. Of the 12 insulin-treated patients, 10 received insulin alone and 2 received an oral hypoglycemic agent. Of the 12 non-insulin-treated patients, 7 were treated with an oral hypoglycemic agent. Thus, four groups of six patients were generated. Patients in Groups 1 and 2 received insulin. Patients in Groups 3 and 4 did not receive insulin. Patients in Groups 1 and 3 were treated with a 5-hour infusion of 100 µg/h AC137 on Study Day 2 followed by a 15-hour washout period and a 5-hour infusion of placebo on Study Day 3. Patients in Groups 2 and 4 were treated with a 5-hour infusion of placebo on Study Day 2 followed by a 15-hour washout period and a 5-hour infusion of 100 µg/h AC137 on Study Day 3. Both AC137 and placebo were administered with an intravenous microinfusion pump. All patients consumed a standardized SUSTACAL® oral supplement test meal (7 kcal/kg) 60 minutes after the start of study drug infusion on both treatment days. The SUSTACAL® oral supplement test meal is a commercially available nutritional supplement which contains 1.01 kcal/ml with the caloric composition being 24% protein, 21% fat and 55% carbohydrate. Sodium and calcium caseinates along with soy protein provide the protein calories; partially hydrogenated soybean oil provides the fat calories; and sucrose and corn syrup provide the carbohydrate calories.

Each patient's usual insulin and/or oral hypoglycemic agent and caloric intake, as documented during the screening visit, were stabilized during the 24-hour acclimatization period (Study Day 1). Patients were served breakfast at 8:00 a.m., lunch at 12:00 noon, and dinner at 6:00 p.m. The patient's usual dose of insulin and/or hypoglycemic agent was taken 30 minutes prior to meals. An evening snack was served based on the usual diet of the patients. Water was given as needed. All patients followed this insulin/oral hypoglycemic and dietary regimen throughout the investigation period.

Mean plasma glucose levels from Hours 1 through 5 following a SUSTACAL® supplement test meal are presented in Table 1.

TABLE 1

Mean Plasma Glucose Levels From Hours 1 Through 5 Following a SUSTACAL ® Oral Supplement

| | Mean ± SEM (mg/dl) | | |
|---|---|---|---|
| Subgroup | AC137 | Placebo | p-Value[a] |
| Insulin-Treated Patients (N = 12) | 183.1 ± 13.4 | 243.0 ± 16.5 | 0.0035 |
| Non-Insulin-Treated Patients (N = 12) | 169.8 ± 15.7 | 183.2 ± 19.9 | NS |

[a]P-value for two-period crossover ANOVA.
NS = Not significant.

The mean plasma glucose levels from Hours 1 through 5 were statistically significantly lower following the Sustacal® test meal when insulin-treated patients received AC137 compared to when insulin-treated patients receiving placebo. There was a mean reduction in glucose levels of 23% in AC137-infused insulin-treated patients.

The mean glucose levels were not statistically significantly different in AC137-infused non-insulin-treated patients compared to placebo-treated patients.

The zero-hour $AUC_{glucose(1-5)}$ (area under the plasma glucose concentration curve, above or below the baseline plasma glucose concentration, between hours 1 and 5 of the test period calculated employing the trapezoidal rule) and zero-hour $C_{max}$ for plasma glucose (maximum plasma glucose concentration) in insulin-treated and non-insulin-treated patients following a SUSTACAL® oral supplement test meal are summarized in Table 2.

TABLE 2

Zero-Hour $AUC_{(1-5)}$ and Zero-Hour $C_{max}$ Following a
SUSTACAL ® Oral Supplement Test Meal: Plasma Glucose

| Subgroup/Parameter | AC137 (Mean ± SEM) | Placebo (Mean ± SEM) | p-Value[a] |
|---|---|---|---|
| Insulin-Treated Patients (N = 12) | | | |
| $AUC_{(1-5)}$ (mg-h/dl) | 51.2 ± 52.0 | 284.4 ± 52.3 | 0.0012 |
| $C_{max}$ (mg/dl) | 42.0 ± 15.0 | 118.1 ± 17.1 | 0.0007 |
| Non-Insulin-Treated Patients (N = 12) | | | |
| $AUC_{(1-5)}$ (mg-h/dl) | 53.3 ± 27.4 | 124.3 ± 28.3 | NS |
| $C_{max}$ (mg/dl) | 40.1 ± 10.2 | 66.9 ± 7.7 | 0.038 |

[a]P-value for two period crossover ANOVA.
NS = Not significant.

The $AUC_{(1-5)}$ and $C_{max}$ for plasma glucose in insulin-treated and non-insulin-treated patients following a Sustacal® test meal are summarized in Table 3.

TABLE 3

$AUC_{(1-5)}$ and $C_{max}$ Following a
SUSTACAL ® Oral Supplement Test Meal: Plasma Glucose

| Subgroup/Parameter | AC137 (Mean ± SEM) | Placebo (Mean ± SEM) | p-Value[a] |
|---|---|---|---|
| Insulin-Treated Patients (N = 12) | | | |
| $AUC_{(1-5)}$ (mg-h/dl) | 736.2 ± 54.1 | 984.7 ± 67.6 | 0.0031 |
| $C_{max}$ (mg/dl) | 213.3 ± 14.9 | 293.2 ± 21.9 | 0.0017 |
| Non-Insulin-Treated Patients (N = 12) | | | |
| $AUC_{(1-5)}$ (mg-h/dl) | 681.3 ± 62.8 | 738.3 ± 80.0 | NS |
| $C_{max}$ (mg/dl) | 197.1 ± 17.1 | 220.4 ± 20.0 | 0.048 |

[a]P-value for two period crossover ANOVA.
NS = Not significant.

Glucose zero-hour $AUC_{(1-5)}$, zero-hour $C_{max}$, $AUC_{(1-5)}$, and $C_{max}$ were statistically significantly lower when when insulin-treated patients received AC137 compared to when insulin-treated patients received placebo. The effect was most pronounced for the zero-hour parameters. There was a mean reduction of 93% in zero-hour $AUC_{(1-5)}$ and a mean reduction of 66% in zero-hour $C_{max}$ when insulin-treated patients received AC137.

In non-insulin-treated patients, only glucose zero-hour $C_{max}$ and $C_{max}$ were statistically significantly lower with AC137 infusion, although the reduction in zero-hour $AUC_{(1-5)}$ appears to be clinically meaningful.

Results from insulin-treated patients and non-insulin-treated patients were compared (ANOVA). After placebo infusion, glucose zero-hour $AUC_{(1-5)}$ was 2.3-fold higher (p=0.013) in insulin-treated patients than in non-insulin-treated patients. Glucose zero-hour $C_{max}$ was 1.8-fold higher (p=0.012) in insulin-treated placebo patients than in non-insulin-treated placebo patients. Glucose $AUC_{(1-5)}$ and $C_{max}$ also were high in insulin-treated placebo patients (p=0.028 and 0.023, respectively). When results from insulin-treated and non-insulin-treated patients were compared (ANOVA) after AC137 infusion, there was no statistically significant difference for glucose zero-hour $AUC_{1-5)}$, zero-hour $C_{max}$, $AUC_{(1-5)}$, and $C_{max}$.

The patient selection criteria included Type II diabetic patients with levels of glycosylated hemoglobin ($HbA_{1c}$) up to 13%, and, a correlation between AC137-induced reduction in postprandial hyperglycemia and entry $HbA_{1c}$ levels was determined. Reduction in postprandial hyperglycemia was calculated by subtracting glucose zero-hour $AUC_{(1-5)}$ with AC137 infusion from placebo infusion zero-hour $AUC_{(1-5)}$. The results are presented in FIG. 1 with patients rank-ordered for $HbA_{1c}$ levels.

Figure 1:
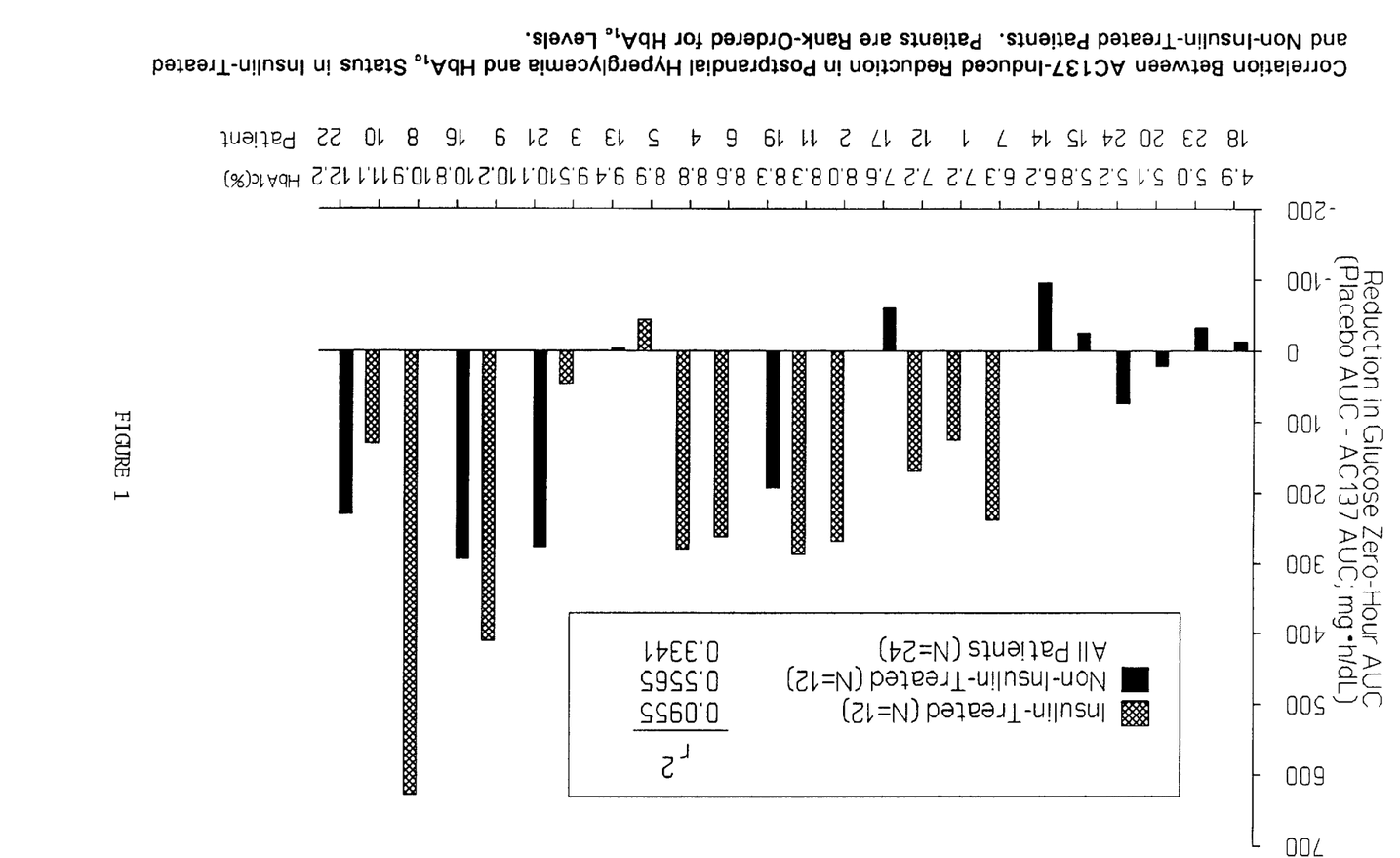
FIG. 1 shows the correlation between AC137-induced reduction in post-prandial hyperglycemia and HbA1c status in insulin-treated and non-insulin-treated patients. Patients are rank-ordered for HbA1c levels. The correlation ($r^2$) was 0.56 in non-insulin-treated patients, 0.10 in insulin-treated patients, and 0.33 for all patients combined.

The reduction in postprandial hyperglycemia appeared to increase with $HbA_{1c}$ levels in non-insulin-treated patients. The correlation ($r^2$) was 0.56 in this subgroup of patients, 0.10 in insulin-treated patients, and 0.33 for all patients combined.

In order to further evaluate the relationship of the reduction in postprandial hyperglycemia to $HbA_{1c}$ levels, glucose zero-hour $AUC_{(1-5)}$, zero-hour $C_{max}$, $AUC_{(1-5)}$, and $C_{max}$ following a Sustacal® test meal were evaluated in insulin-treated and non-insulin-treated patients with $HbA_{1c}$ levels ≧8% and <8%.

For patients with $HbA_{1c}$ levels ≧8%, the zero-hour $AUC_{(1-5)}$ and zero-hour $C_{max}$ for plasma glucose in insulin-treated and non-insulin-treated patients following a Sustacal® test meal are summarized in Table 4.

TABLE 4

Zero-Hour $AUC_{(1-5)}$ and Zero-Hour $C_{max}$ Following a
SUSTACAL ® Supplement Test Meal: Plasma Glucose in Patients
With $HbA_{1c}$ Levels ≧ 8%

| Subgroup/Parameter | AC137 (Mean ± SEM) | Placebo (Mean ± SEM) | p-Value[a] |
|---|---|---|---|
| Insulin-Treated Patients (N = 9) | | | |
| $AUC_{(1-5)}$ (mg-h/dl) | 63.1 ± 69.4 | 314.8 ± 67.3 | 0.0080 |
| $C_{max}$ (mg/dl) | 48.8 ± 19.4 | 127.1 ± 21.4 | 0.0055 |
| Non-Insulin-Treated Patients (N = 5) | | | |
| $AUC_{(1-5)}$ (mg-h/dl) | −7.9 ± 32.8 | 189.8 ± 41.2 | 0.0323 |
| $C_{max}$ (mg/dl) | 20.6 ± 12.0 | 79.4 ± 11.2 | 0.0238 |

[a]P-value for two period crossover ANOVA.
NS = Not significant.

For patients with $HbA_{1c}$ levels ≧8%, the $AUC_{(1-5)}$ and $C_{max}$ for plasma glucose in insulin-treated and non-insulin-treated patients following a SUSTACAL® oral supplement test meal are summarized in Table 5.

TABLE 5

AUC$_{(1-5)}$ and C$_{max}$ Following a SUSTACAL ® Supplement Test Meal: Plasma Glucose in Patients With HbA$_{1c}$ Levels ≥ 8%

| Subgroup/Parameter | AC137 (Mean ± SEM) | Placebo (Mean ± SEM) | p-Value[a] |
|---|---|---|---|
| Insulin-Treated Patients (N = 9) | | | |
| AUC$_{(1-5)}$ (mg-h/dl) | 747.9 ± 68.6 | 987.7 ± 75.4 | 0.0337 |
| C$_{max}$ (mg/dl) | 220.0 ± 18.6 | 295.3 ± 23.6 | 0.0153 |
| Non-Insulin-Treated Patients (N = 5) | | | |
| AUC$_{(1-5)}$ (mg-h/dl) | 871.4 ± 49.8 | 1033.8 ± 34.3 | 0.0369 |
| C$_{max}$ (mg/dl) | 240.4 ± 16.4 | 290.4 ± 11.4 | 0.0362 |

[a]P-value for two period crossover ANOVA.
NS = Not significant.

For both insulin-treated and non-insulin-treated patients with HbA$_{1c}$ levels ≥8%, glucose zero-hour AUC$_{(1-5)}$, zero-hour C$_{max}$, AUC$_{(1-5)}$, and C$_{max}$ were statistically significantly lower when patients received AC137 compared to when patients received placebo. The differences for non-insulin-treated patients with HbA$_{1c}$ levels ≥8% were statistically significant and were greater than those for all non-insulin-treated patients regardless of HbA$_{1c}$ level.

For patients with HbA$_{1c}$ levels <8%, the zero-hour AUC$_{(1-5)}$ and zero-hour C$_{max}$ for plasma glucose in insulin-treated and non-insulin-treated patients following a SUSTACAL® oral supplement test meal are summarized in Table 6.

TABLE 6

Zero-Hour AUC$_{(1-5)}$ and Zero-Hour C$_{max}$ Following a SUSTACAL ® Oral Supplement Test Meal: Plasma Glucose in Patients With HbA$_{1c}$ Levels < 8%

| Subgroup/Parameter | AC137 (Mean ± SEM) | Placebo (Mean ± SEM) | p-Value[a] |
|---|---|---|---|
| Insulin-Treated Patients (N = 3) | | | |
| AUC$_{(1-5)}$ (mg-h/dl) | 15.5 ± 30.4 | 193.1 ± 14.4 | 0.0324 |
| C$_{max}$ (mg/dl) | 21.7 ± 10.8 | 91.0 ± 20.6 | NS |
| Non-Insulin-Treated Patients (N = 7) | | | |
| AUC$_{(1-5)}$ (mg-h/dl) | 96.9 ± 32.8 | 77.6 ± 29.0 | NS |
| C$_{max}$ (mg/dl) | 54.0 ± 13.4 | 58.0 ± 9.8 | NS |

[a]Two-period crossover ANOVA.
NS = Not significant.

For patients with Hb$_{A1c}$ levels <8%, the AUC$_{(1-5)}$ and C$_{max}$ for plasma glucose in insulin-treated and non-insulin-treated patients following a SUSTACAL® oral supplement test meal are summarized in Table 7.

TABLE 7

AUC$_{(1-5)}$ and C$_{max}$ Following a Sustacal ® Test Meal: Plasma Glucose in Patients With HbA$_{1c}$ Levels < 8%

| Subgroup/Parameter | AC137 (Mean ± SEM) | Placebo (Mean ± SEM) | p-Value[a] |
|---|---|---|---|
| Insulin-Treated Patients (N = 3) | | | |
| AUC$_{(1-5)}$ (mg-h/dl) | 700.8 ± 84.2 | 975.8 ± 179.7 | NS |
| C$_{max}$ (mg/dl) | 193.0 ± 22.1 | 286.7 ± 61.9 | NS |
| Non-Insulin-Treated Patients (N = 7) | | | |
| AUC$_{(1-5)}$ (mg-h/dl) | 545.5 ± 61.9 | 527.3 ± 41.8 | NS |
| C$_{max}$ (mg/dl) | 166.1 ± 20.3 | 170.4 ± 13.9 | NS |

[a]Two-period crossover ANOVA.
NS = Not significant.

For insulin-treated patients with HbA$_{1c}$ levels <8%, only glucose zero-hour AUC$_{(1-5)}$ was statistically significantly lower when patients received AC137 compared to when patients received placebo, although the differences for glucose zero-hour C$_{max}$, AUC$_{(1-5)}$, and C$_{max}$ may be clinically beneficial. For all insulin-treated patients regardless of HbA$_{1c}$ level, glucose zero-hour AUC$_{(1-5)}$, zero-hour C$_{max}$, AUC$_{(1-5)}$, and C$_{max}$ were statistically significantly lower when patients received AC137 compared to when patients received placebo. For non-insulin-treated patients with HbA$_{1c}$ levels <8%, glucose zero-hour AUC$_{(1-5)}$, zero-hour C$_{max}$, AUC$_{(1-5)}$, and C$_{max}$ when patients received AC137 compared to when patients received placebo were not significantly different.

Thus, administration of an amylin agonist beneficially decreases blood glucose concentrations in patients with Type II diabetes even when such patients are not taking insulin, that is, for example, when such patients have not experienced primary dietary failure, particularly patients with Type II diabetes who have above-normal HbA1c values.

What is claimed is:

1. A method for the treatment of a non-insulin-taking Type II diabetic subject comprising administering to said subject a therapeutically effective amount of an amylin agonist.

2. A method of lowering blood glucose in a non- insulin-taking Type II diabetic subject comprising administering to said subject a blood-glucose-lowering amount of an amylin agonist.

3. A method according to claim 1 wherein said subject has a HbA1c value above about the upper end of the of range of HbA1c values for normal subjects.

4. A method according to claim 2 wherein said subject has an HbA1c value above about the upper end of the range of HbA1c values for normal subjects.

5. A method according to claim 1 wherein said subject has an HbA1c value of about 8% or above.

6. A method according to claim 2 wherein said subject has an HbA1c value of about 8% or above.

7. A method according to any of claims 1–6 wherein said amylin agonist is [25,28,29]Pro-h-amylin.

8. A method according to any of claims 1–6 wherein said amylin agonist is s-calcitonin.

9. A method according to any of claims 1–6 wherein said amylin agonist is h-amylin.

10. A method according to claim 1 wherein said amylin agonist is administered intramuscularly or subcutaneously.

11. A method according to claim 2 wherein said amylin agonist is administered intramuscularly or subcutaneously.

12. A method according to claim 7 wherein said amylin agonist is administered intramuscularly or subcutaneously.

13. A method according to any of claims 1–6 wherein said amylin agonist is selected from the group consisting of $^{18}$Arg$^{25,28}$Pro-h-amylin, des-$^{1}$Lys$^{18}$Arg$^{25,28}$Pro-h-amylin, $^{18}$Arg$^{25,28,29}$Pro-h-amylin, des-$^{1}$Lys-$^{18}$Arg-$^{25,28,29}$Pro-h-amylin, des-$^{1}$Lys$^{25,28,29}$Pro-h-amylin, and $^{25}$Pro$^{26}$Val$^{25,28}$Pro-h-amylin.

14. A method for the treatment of a non-insulin-taking Type II diabetic subject comprising administering to said subject a therapeutically effective amount of a medicine comprising $^{25,28,29}$Pry-h-amylin.

15. The method of claim 14 wherein said medicine is administered in an amount which comprises from about 1.0 μg/kg/day $^{25,28,29}$Pro-h-amylin to about 4.0 μg/kg/day $^{25,28,29}$Pro-h-amylin in a single or divided doses.

16. The method of claim 14 wherein said medicine is administered in an amount which comprises from about 1.0 μg/kg/day $^{25,2829}$Pro-h-amylin to about 6.0 μg/kg/day $^{25,28,29}$Pro-h-amylin in a single or divided doses.

17. The method of any of claims 14, 15 or 16 wherein said subject has an HbA1c value of about 8% or above.

18. The method of any of claims 14, 15 or 16 wherein said $^{25,28,29}$Pro-h-amylin is an acetate salt of $^{25,28,29}$Pro-h-amylin.

19. The method of any of claims 14, 15 or 16 wherein said $^{25,28,29}$Pro-h-amylin is a hydrochloride salt of $^{25,28,29}$Pro-h-amylin.

20. A method of lowering post-prandial blood glucose in a non-insulin-taking Type II diabetic subject comprising administering to said subject a post-prandial blood glucose lowering amount of an amylin agonist.

21. The method of claim 20 wherein said amylin agonist is $^{25,28,29}$Pro-h-amylin.

* * * * *